United States Patent
Allman et al.

(10) Patent No.: US 7,549,745 B2
(45) Date of Patent: Jun. 23, 2009

(54) APPARATUS AND METHOD FOR CORRECTING FOR ABERRATIONS IN A LENS SYSTEM

(75) Inventors: Brendan Edward Allman, East Brunswick (AU); Keith Nugent, North Fitzroy (AU)

(73) Assignee: Iatia Imaging Pty Ltd, Victoria (AU)

( * ) Notice: Subject to any disclaimer, the term of this patent is extended or adjusted under 35 U.S.C. 154(b) by 375 days.

(21) Appl. No.: 10/597,255

(22) PCT Filed: Jan. 11, 2005

(86) PCT No.: PCT/AU2005/000020

§ 371 (c)(1),
(2), (4) Date: Jul. 18, 2006

(87) PCT Pub. No.: WO2005/073689

PCT Pub. Date: Aug. 11, 2005

(65) Prior Publication Data

US 2008/0225227 A1    Sep. 18, 2008

(30) Foreign Application Priority Data

Feb. 2, 2004    (AU) ............................... 2004900487

(51) Int. Cl.
*A61B 3/14*    (2006.01)
(52) U.S. Cl. .................. 351/206; 351/221; 351/246
(58) Field of Classification Search .......... 351/206, 351/246, 209, 210, 221, 200, 205
See application file for complete search history.

(56) References Cited

U.S. PATENT DOCUMENTS

| 6,331,059 | B1 | 12/2001 | Kudryashov et al. |
| 6,361,170 | B1 | 3/2002 | Bille |
| 6,609,794 | B2 * | 8/2003 | Levine .................. 351/221 |

FOREIGN PATENT DOCUMENTS

| WO | WO 98/27863 | 7/1998 |
| WO | WO 00/33250 | 6/2000 |
| WO | WO 02/35995 | 5/2002 |
| WO | WO 03/000153 | 1/2003 |
| WO | WO 03/105678 | 12/2003 |

OTHER PUBLICATIONS

Primot et al., "Deconvolution from wave-front sensing: a new technique for compensating turbulence-degraded images", J. Opt Soc. Am. A., vol. 7, No. 9, Sep. 1990, pp. 1598-1608.

* cited by examiner

*Primary Examiner*—Hung X Dang
(74) *Attorney, Agent, or Firm*—Fish & Richardson P.C.

(57) ABSTRACT

A method and apparatus for compensating for aberrations or distortions of an optical system such as an eye of a patient which is to be imaged by a camera is disclosed. Light passing through the optical system is detected by a charge coupled device (62) via an imaging system (60). Phase data relating to the light passing through the system is determined and a processor (64) processes the data so that a transformation is determined which transforms the data relating to the wavefront of the light so that the phase data is transformed to remove aberrations or distortions introduced by the optical system. Thus, clearer images of the fundus of an eye generated by light passing through the optical system of the eye and for determining distortions or aberrations introduced by the optical system of the eye are provided.

17 Claims, 5 Drawing Sheets

APPARATUS AND METHOD FOR CORRECTING FOR ABERRATIONS IN A LENS SYSTEM

FIELD OF THE INVENTION

This invention relates to an apparatus and method for compensation for aberrations in a lens system and, in one particular arrangement, relates to a fundus camera for taking images of the fundus of a person's eye. The invention also relates to a method and apparatus for determining aberrations of a lens system.

BACKGROUND OF THE INVENTION

As is well known, optical systems are used in many environments in order to focus light. Many optical systems include imperfections which can introduce distortions or aberrations into the focusing of the light which reduces resolution and image quality. This occurs not only in mechanical systems which include manufactured lenses made from glass and other materials, but also in biological specimens such as the human eye. The present invention has particular application to compensating for aberrations caused by imperfections of the "lensing system" of a human eye comprising the cornea and eye lens, and in particular to a fundus camera including such an apparatus which can be used to take images of the fundus of a human eye for diagnosis and treatment purposes.

Fundus cameras are known and are used to examine the fundus or back of a person's eye. In general, the fundus camera comprises a microscope and a camera. The camera directs a beam of light into a person's eye and light reflected from the fundus is captured so that an image of the fundus can be obtained. The resolution of the image of the fundus is limited by the optical quality of the person's eye and, in particular, by distortions or aberrations which may be introduced by virtue of the light passing through the cornea and lens of the eye. In one known fundus camera, light from a person's eye is reflected by a deformable mirror to a charge coupled device for producing an image of the fundus. The charge coupled device is connected to a processor which in turn manipulates the deformable mirror to compensate for distortions which are introduced by the optical system of the eye so as to improve resolution. In order to control the deformable mirror, light is shone into the eye, reflected from a point on the back surface and then passes through a lenslet array which provides light beams of known spatial orientation which are then detected and their position relative to a reference grid determined. The deformable mirror is moved by the processing system so as to compensate for the distortions or aberrations introduced by the optics of the eye, as measured against the reference grid, to improve resolution. While current technology provides general details of the retina for clinical diagnosis of retinal diseases, resolution is still limited.

Improving resolution of images obtained by a fundus camera, and which compensate for distortions or aberrations introduced by the optics of the eye is extremely important when attempting to diagnose retinal diseases such as retinopathy and glaucoma. The earlier diagnosis of glaucoma is particular important because glaucoma is a disease in which the retina deteriorates as a result, for example, of increased pressure within the eye. The effects of glaucoma are not noticed by the sufferer until the disease had become irreversible. Current techniques use optical field testing and fundus cameras to detect glaucoma after damage has already occurred.

If resolution of fundus cameras can be improved, the possibility exists that images with detail not currently possible, including structures such as rods and cones of the fundus, currently not visible without dissection, can be obtained. The ability to obtain such images will greatly improve diagnosis of retinal diseases and early treatment.

SUMMARY OF THE INVENTION

The object of the invention is therefore to provide a method and apparatus for compensation for distortions or aberrations of an optical system and, in particular, to a fundus camera including such apparatus, which will enable better images to be obtained.

The invention, in a first aspect, may be said to reside in an apparatus for compensation for aberrations or distortions of an optical system, comprising:
  means for directing a beam of light through the optical system;
  detector means for detecting the beam of light after the beam of light has passed through the optical system; and
  processing means for receiving data from the detector and for processing the data to produce phase data relating to the wavefront of the beam of light emanating from the optical system to enable a transformation to be determined for transforming the data relating to the detected image to a predetermined reference, and for applying the transformation to image data which has passed through the optical system to remove aberrations or distortions introduced by the optical system.

Thus, according to the present invention the apparatus produces a transformation which transforms data relating to an image and which passes through the optical system to compensate for aberrations and distortions in the system. Thus, when an article is viewed through the system and an image obtained, the data can be manipulated in accordance with the transformation to remove the effects of the aberration or distortion so that a true image of the object, without the distortions or aberrations introduced by the systems, can be obtained. Since the transformation is provided to the actual data which produces the image to correct that data, the entire data which is captured to produce an image can be corrected and resolution of the captured image greatly improved.

In the preferred embodiment of the invention the phase data relating to the wavelength is determined in accordance with the algorithm set out in International Patent Application No. PCT/AU99/00949, owned by The University of Melbourne, the content of which is incorporated into this specification by this reference. This algorithm produces phase data for enabling a phase image of an article to be produced. This algorithm solves the transport of intensity equation in order to produce the phase data from which the phase image can be created.

Preferably the data to which the transformation is applied is intensity data. However, in other embodiments, the data may be phase data relating to an image or a combination of intensity data and phase data.

In one embodiment of the invention the application of the transformation comprises a deconvolution of the intensity data.

In a still further embodiment the transformation is a propagation of the wave from one image location to another.

Preferably the detector comprises a charge coupled device.

Preferably the apparatus includes a light source for shining a parallel beam of light through the optical system and a beam splitter for directing reflected light from an article travelling back through the optical system to the detector for detection.

Preferably the apparatus includes a lens for focusing light passing through the optical system so as to obtain an image of an article viewed through the optical system.

The invention may also be said to reside in a method for compensating for aberrations or distortions in an optical system, comprising the steps of:

shining light through the optical system;

detecting the light after the light has passed through the optical system;

producing phase data relating to the wavefront of light detected by the detector;

determining a transformation to transform the data in accordance with a known reference data; and applying the transformation to data relating to an image of an article produced through the optical system so as to remove the effects of aberrations or distortions of the optical system on that data.

Preferably the data to which the transformation is applied is data relating to the image of the object so that the image of the object is produced free of distortions which would otherwise be introduced by the distortions or aberrations in the lens system.

Preferably the detector comprises a charge coupled device.

Preferably the data relating to the image is captured by directing a beam of light through apparatus including a lens for focusing light passing through the optical system so as to obtain an image of an article viewed through the optical system.

The invention may also be said to reside in a fundus camera for producing an image of the fundus of a person's eye, said camera comprising:

a detector for detecting a beam of light passing through the cornea and lens of a person's eye and reflected from the fundus of the person's eye and again passing through the lens and cornea of the person's eye;

processing means for determining phase data relating to the wavefront of the light beam detected by the detector and for producing a transformation required to convert the data from that detected by the detector to a known reference data;

the detector also being for detecting a beam of light directed through a person's eye to obtain an image of the fundus and for producing data relating to that image; and the processing means being for processing the data relating to the image in accordance with the transformation to transform the data relating to the image to compensate for aberrations and distortions introduced by the cornea and lens of the person's eye, and for producing an image of the fundus, which is therefore free of distortions and aberrations introduced by the cornea and lens of the person's eye.

Preferably the camera also includes a light source for producing the beams of light detecting by the detector.

Preferably the camera further includes a lens for focusing the beam of light towards the eye so that the beam of light which produces the image is reflected from the fundus so as to provide an image of the fundus.

The camera may also include a monitor for displaying a phase image of the fundus.

A further aspect of the invention relates to an apparatus for determining the amount of aberration or distortion of a lens system.

This aspect of the invention may be said to reside in apparatus for determining the amount of distortion or aberration of a lens system, comprising:

means for directing a beam of light through the optical system;

detector means for detecting the beam of light after the beam of light has passed through the optical system; and processing means for receiving data from the detector and for processing the data to produce phase data relating to the wavefront of the beam of light emanating from the optical system and for determining the amount of aberration or distortion of the lens system relative to reference phase data.

Thus, the amount of aberration or distortion introduced by the lens system can therefore be determined. This aspect has application in determining the amount of aberration or distortion of a lens system such as the cornea and lens of an eye to enable treatment of the cornea and lens to be performed or to facilitate the prescription of spectacles or contact lenses to correct for distortions and aberrations introduced by the cornea and lens of a person's eye.

This aspect of the invention may also be said to reside in a method for determining aberrations or distortions in an optical system, comprising the steps of:

shining light through the optical system;

detecting the light after the light has passed through the optical system;

producing phase data relating to the wavefront of light detected by the detector; and comparing the phase data with a reference phase data to determine the difference and therefore the aberration or distortions introduced by the lens system.

In the preferred embodiment of this aspect of the invention, the optical system is a person's eye and the reference phase data is phase data obtained from reflection from the back of a person's eye. Thus, when light is shone through the person's eye and detected, distortions introduced by the cornea and lens can be measured compared to a known distortion-free wavefront produced by the spherical shape of the back of the eye and which would be reflected from the back of the eye and through the eye if there are no distortions introduced by the eye.

BRIEF DESCRIPTION OF THE DRAWINGS

A preferred embodiment of the invention will be described, by way of example, with reference to the accompanying drawings in which.

DETAILED DESCRIPTION OF THE PREFERRED EMBODIMENT

The preferred embodiment of the invention will be described with reference to a fundus camera which removes distortions and aberrations introduced by the optics of a human eye from an image of the fundus of the human eye. However, it will be appreciated that the invention has broader application and could be used in other biological environments or in mechanical environments for compensating for distortions of an image caused by distortions or aberrations introduced by an optical system used to produce the image.

Figure 1:
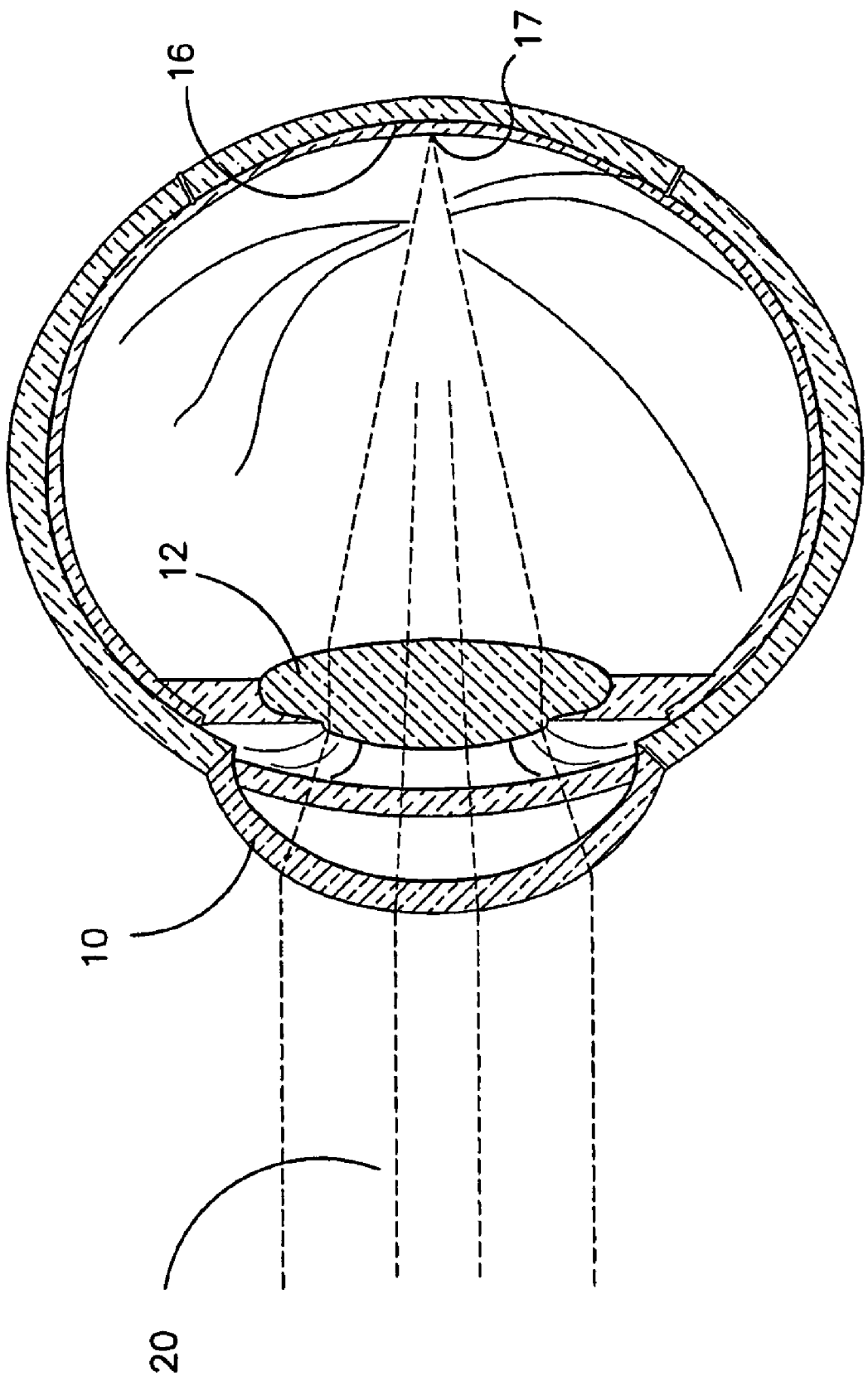
FIG. 1 is a view of a human eye.

FIG. 1 shows a drawing of a human eye in which the cornea 10, lens 12 and fundus 16 (which is generally the back of the eye) can be seen. When a beam of light enters the human eye as illustrated by beam 20 in FIG. 1, the beam is focused by the cornea and the lens onto the fundus so as to create an image 17 of an object which the eye is viewing.

Figure 2:
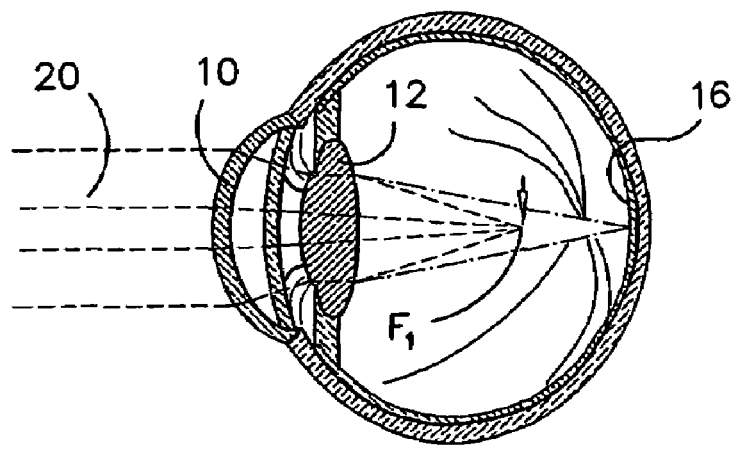
FIG. 2, FIG. 3 and FIG. 4 show various distortions or aberrations which can be introduced into light passing through the human eye and imaging on the fundus of the human eye.
Figure 3:
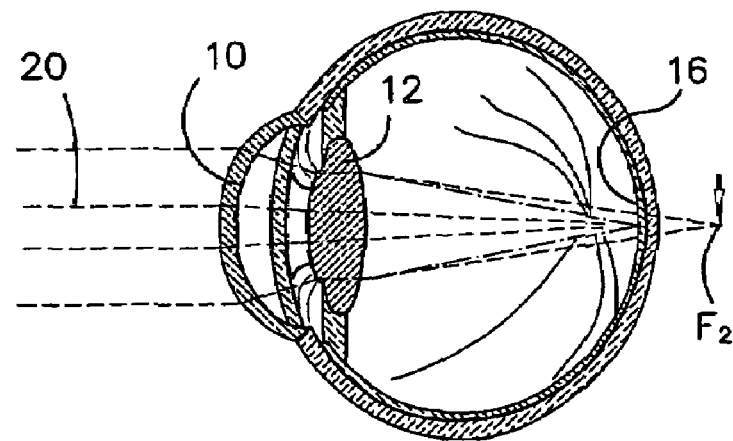
Figure 4:
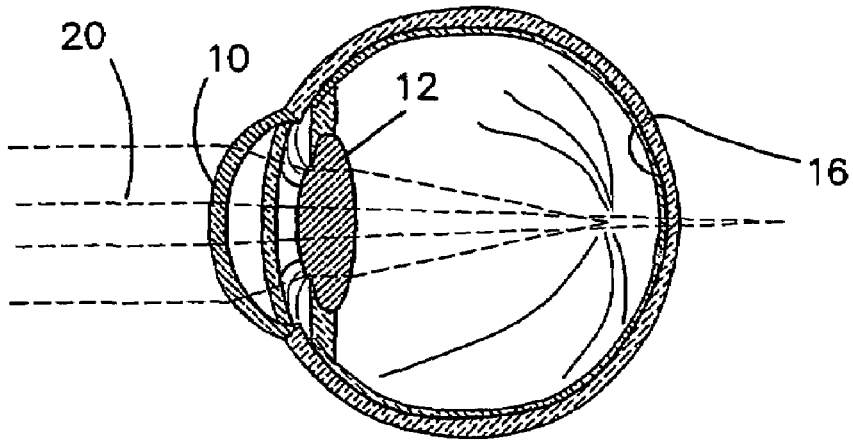

As is well known, common ailments, such as myopia, hyperopia and astigmatism, cause blurring of the image captured by the eye and which is generally corrected by surgical techniques or by wearing glasses or contact lenses. FIG. 2 shows an example of where the eye is myopic and the light beam 20 is focused by the cornea 10 and lens 12 at a position before the fundus 16, and which is marked F1 in FIG. 2. FIG. 3 shows a situation where the eye suffers from hyperopia in which the image F2 is focused after the fundus 16, and FIG. 3 shows astigmatism in which various axes of the cornea 10 and lens 12 focus differently so as to produce a distorted image on the fundus 16.

When a fundus camera is used to produce an image of the fundus for diagnosis purposes and possible treatment, the image which is captured by the fundus camera is distorted by any distortion or aberration introduced by the cornea and lens 12 of the person's eye. These distortions greatly reduce the resolution of the image and make it impossible to see fine details such as the cones and rods of the fundus. Thus, diagnosis of diseases which effect the fundus such as glaucoma and retinopathy is made more difficult. In view of this, structural detail of the cones and rods of a person's eye can generally only be ascertained by a surgical procedure.

The fundus camera of the present invention compensates for distortions and aberrations introduced by the cornea and lens of the eye so as to improve the resolution of an image of the fundus to enable fine detail such as the detail of the rods and cones to be observed. The fundus camera 50 shown in FIG. 5 comprises a light source 52 for producing a beam of light 54, a beam splitter 56, which enables the beam of light 54 to pass through the beam splitter 56, to a person's eye E. The apparatus may include a conventional support against which a person rests his or her head so as to locate the eye in the required position so that the beam of light 54 can be directed into the person's eye E. Such supports and peripheral structure of the fundus camera are well known and therefore will not be described in any detail herein. The fundus camera includes a lens 58 which exemplifies an optical system for focusing the beam of light 54' which passes through the splitter 56. The lens 58 is moveable in the direction of double-headed arrow A on a translation stage (not shown) into and out of the path of the beam of light 54' for the reasons which will be described in detail hereinafter.

When light enters the eye E, it passes through the cornea and lens and reflects off the fundus which is at the back of the eye and then again passes through the lens and cornea to the beam splitter 56. The beam splitter 56 splits the light so that the light emanating from the eye travels along path 59 through an imaging system 60 onto detector 62, which is preferably a charge coupled device. The charge coupled device 62 is connected to a processor 64, which may in turn be connected to a monitor 66 for displaying an image of the fundus of the human eye. The processor 64 is also connected to conventional input devices such as a keyboard and the like.

The imaging system 60 may comprise a series of lenses or like devices. The purpose of the imaging system 60 is to enable images to be focused relative to the charge coupled device 62 for obtaining data to enable the transport of intensity equation to be solved and most typically results in images being focused relative to the charge coupled device at three different focal planes, one of which is at the charge coupled device 62 and the other two of which are on either side of the focal plane so as to provide defocused images. These images provide the data for solving the transfer of intensity equation in accordance with the algorithm disclosed in the above-mentioned International application.

The data detected by the charge coupled device 62 is fed to the processor 64 which carries out the algorithm to produce the phase data for enabling a phase image of the object, in this embodiment the fundus of the eye, to be produced. The phase image can be retained in electric format in the processor 64 or displayed on a monitor 66.

Figure 6:
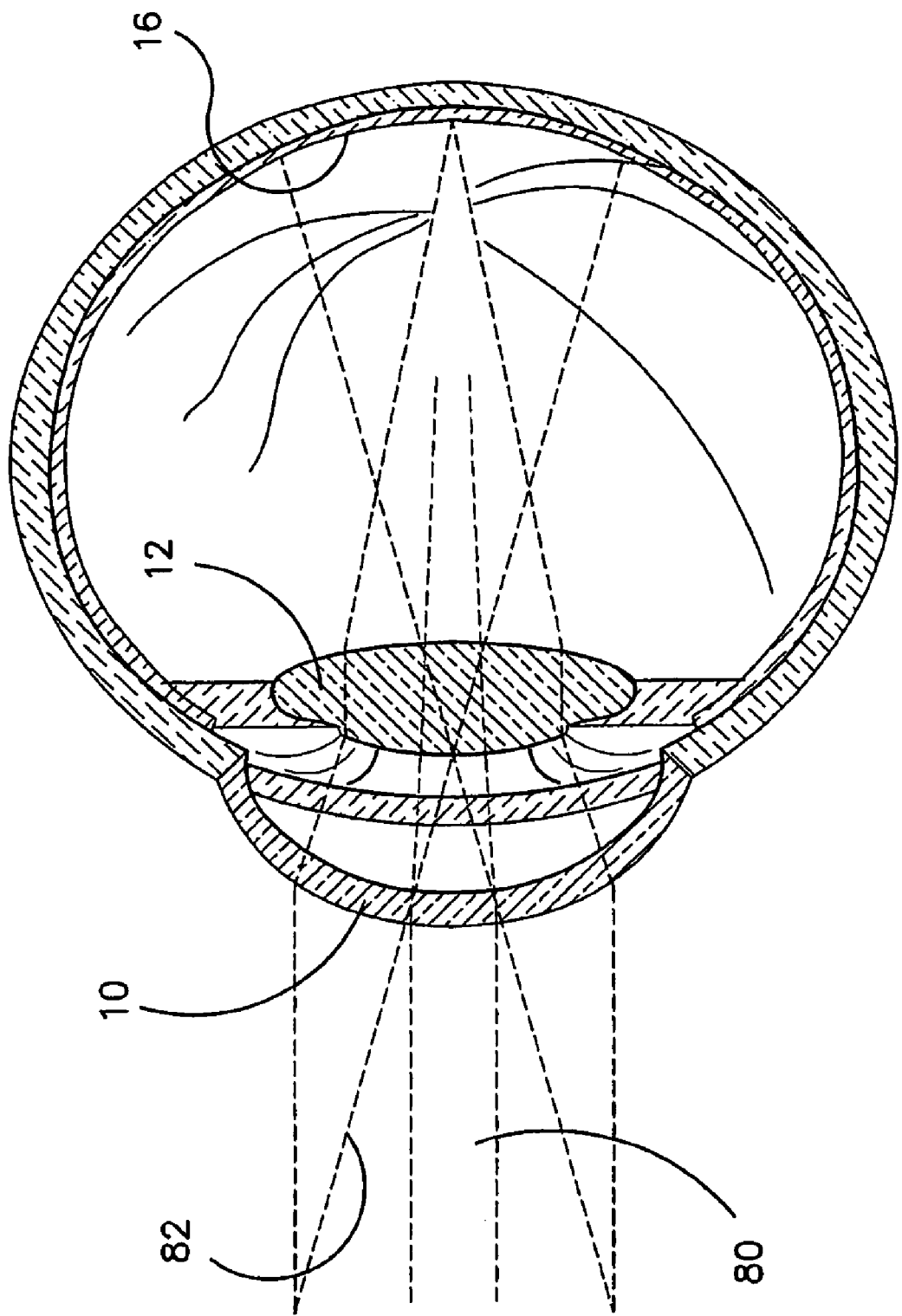
FIG. 6 is a view similar to FIG. 1 showing light beams directed into the eye for producing an image of the fundus which is free from distortions and aberrations introduced by the cornea and lens of the eye.

In order to compensate for aberrations or distortions introduced by the optics of the eye and namely the cornea 10 and lens 12, and also any aberrations or distortions which are included in the lens 58 in the imaging system 60, the lens 58 is first translated in the direction of doubled-headed arrow A out of the path of the beam 54' so that the light source 52 produces a parallel beam of light which is directed to the eye E as shown by the beam of light 80 in FIG. 6. The parallel beam of light 80 is focused by the cornea 10 and the lens 12 of the eye onto the fundus 16 to produce a spot image on the fundus 16. The light is reflected back from the fundus so as to produce a parallel beam of light 80 travelling back to the beam splitter 56 and which is directed by the beam splitter 56 along path 59, through the imaging system 60 and onto the charge coupled device 62. The imaging system 60 is manipulated so as to produce the three images referred to above, namely the in focus image and the two defocused images on the charge coupled device 62, to produce the data which is then supplied to the processor 64 to enable a phase image to be produced. The light reflected from the fundus 16 should therefore be a perfectly spherical wavefront which passes through the lens and cornea to the detector 62 in the manner described above, and form a perfectly planar propagating wavefront. However, if the lens 12 and cornea 10 include any imperfections which would introduce distortions or aberrations into the wavefront such as is the case with myopia, hyperopia and astigmatism as described above, the planar wave beam will be distorted by those conditions or the imperfections in the cornea and the lens. Thus, rather than a planar wavefront being detected by the detector 62, a distorted wavefront is detected by the detector 62.

Because it is expected that if the eye is in perfect condition the wavefront will be planar, phase data relating to a planar wavefront can be used to provide a reference data as to what should be expected to be detected by the detector 62 and produced by the processor 64 once the above-mentioned algorithm is performed to solve the transport of intensity equation to produce the phase data relating to the wavefront reflected from the fundus 16. If the eye is in perfect condition, then the wavefront will produce phase data consistent with a perfectly planar wavefront. However, if distortions or aberrations are introduced, the data will obviously be different and the difference between that data and the planar data can be used to produce a transformation which, when applied to the distorted data, can remove the distortions or aberrations and return that data to the perfect planar wavefront which is expected if no distortions or aberrations are introduced by the lens 12 or cornea 10. When it is desired to produce an image of the fundus for diagnosis or research purposes, the lens 58 is translated in the direction of double-headed arrow A so as to position the lens 58 into the path of the beam 54'. This focuses the beam 54' as shown by beam 82 in FIG. 6 so that the beam 54 is now focused over the entire fundus 16 of the eye.

Light reflected from the fundus travels in the opposite direction through the lens 12, cornea 20, back along the beam path 82 shown in FIG. 6 and is directed by the beam splitter 56 through the imaging system 60 to the detector 62.

The imaging system 60 is then manipulated so as to provide one in focus image enabling data to be supplied to the processor 64 for producing a higher resolution of the fundus 16. The previously determined transformation which was used to transform the distorted wavefront to the planar wavefront and which is already determined by the processor 64, is then applied to the intensity data relating to the actual image of the fundus 16 so as to transform the captured intensity data in accordance with that transformation to remove the effects of distortions and aberrations introduced by the cornea 10 and lens 12 and also any other imperfections in the optical system of the fundus camera 50. One method of this is to use the distorted wave transform to generate a point spread function of the eye caused by distortions or aberrations in the cornea and lens of the eye and perform a deconvolution with the intensity image, thereby producing much better resolution. Furthermore, since the image of the fundus is captured on a charge coupled device 62 and the entirety of the data captured by the charge coupled device 62 is transformed to remove the distortions or aberrations, the improvement in resolution of the image is significant, thereby providing an image which is of sufficient resolution to show details of the cones and rods of the fundus so that diagnosis as well as scientific research relating to the fundus of the human eye can be performed without the need for any invasive technique.

FIGS. 7A to 7E are photographs which show an application of the preferred embodiment of the invention.

Figure 7A:
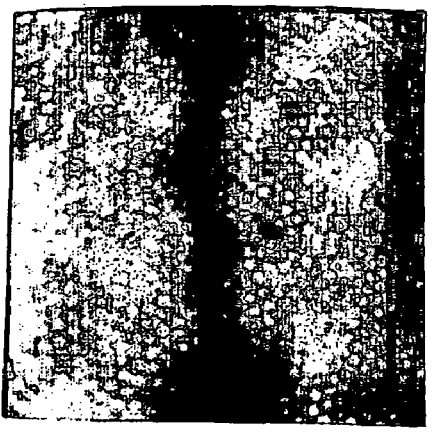
FIGS. 7A, 7B, 7C, 7D and 7B are photographs illustrating the application of the preferred embodiment of the invention.
Figure 7B:
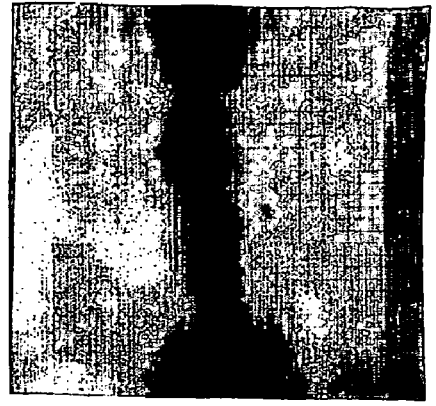

FIG. 7A is intended to represent a true depiction of fundus of a human eye. FIG. 7B is an image which one would expect to obtain if the eye contains some aberrations caused by the lens and cornea as described above. As is apparent, the image in FIG. 7B is very much blurred compared to the depiction in FIG. 7A.

Figure 7C:
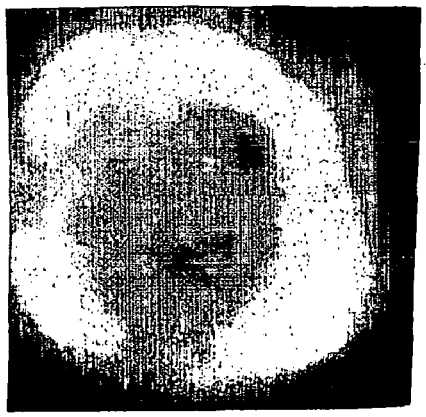
Figure 7D:

FIG. 7C shows phase data which has been created from the image of FIG. 7B by the algorithm previously referred to. If the eye was in perfect condition and a point source emanated from the fundus of the eye, the phase image in FIG. 7C would be a perfect circle. However, because of the distortions, the wavefront itself has been distorted and therefore the image is not perfect. Because it is known that if there is no distortions, a perfect circular image emanating from a point source at the fundus or, in other words, a planar wave, would be received. A transformation can be determined to transfer the phase image in FIG. 7C to what phase image would be expected if there were no aberrations or distortions. In the preferred embodiment of the invention, this is done by a point spread function which is shown in FIG. 7D in which various pixels are provided with various intensities of light corresponding to the phase image of FIG. 7C.

Once again, if the phase image of FIG. 7C was perfect, then only one pixel would be illuminated and the illumination would not have tended to spread to adjacent pixels.

Figure 7E:

Thus, the point spread function provides a transformation which can be used to transfer the blurred image in FIG. 7B to a higher resolution image, as shown in FIG. 7E. This is done by deconvolution of the image of FIG. 7B, where the point spread function of FIG. 7D is effectively subtracted from the image of FIG. 7B to remove the blurriness and distortions so that a much higher resolution is given, as shown by FIG. 7E. In other words, the point spread function can be thought of as being used to divide the blurred image of FIG. 7B in order to remove the distortions to thereby provide the higher resolution figures shown in FIG. 7E.

As will be apparent, the image of FIG. 7E is much closer to the actual image of FIG. 7A than the blurred image of FIG. 7B, and therefore a much better and higher resolution image is obtained by the preferred embodiment of the invention.

Thus, if an image is actually formed by the imaging system, the point spread function is deconvoluted to create an image without the distortion. In another embodiment where a real image is not created, the transformation may be performed by a wave propagator to transform the image data from one plane to another plane so that at the said another plane the distortions or aberrations are removed to thereby provide an image with better resolution.

In the preferred embodiment the transformation is performed on intensity data (i.e. the amplitude of the data which is captured by the imaging system 60).

However, in other embodiments, the transformation may be performed on phase data relating to the image or in a combination of both the phase data and intensity data.

A second aspect of the invention can be used to determine the amount of distortion or aberration introduced by the cornea and lens of a person's eye to provide information which may be useful in surgical treatment of the eye or the determination of a suitable prescription for spectacles or contact lenses.

Figure 5:
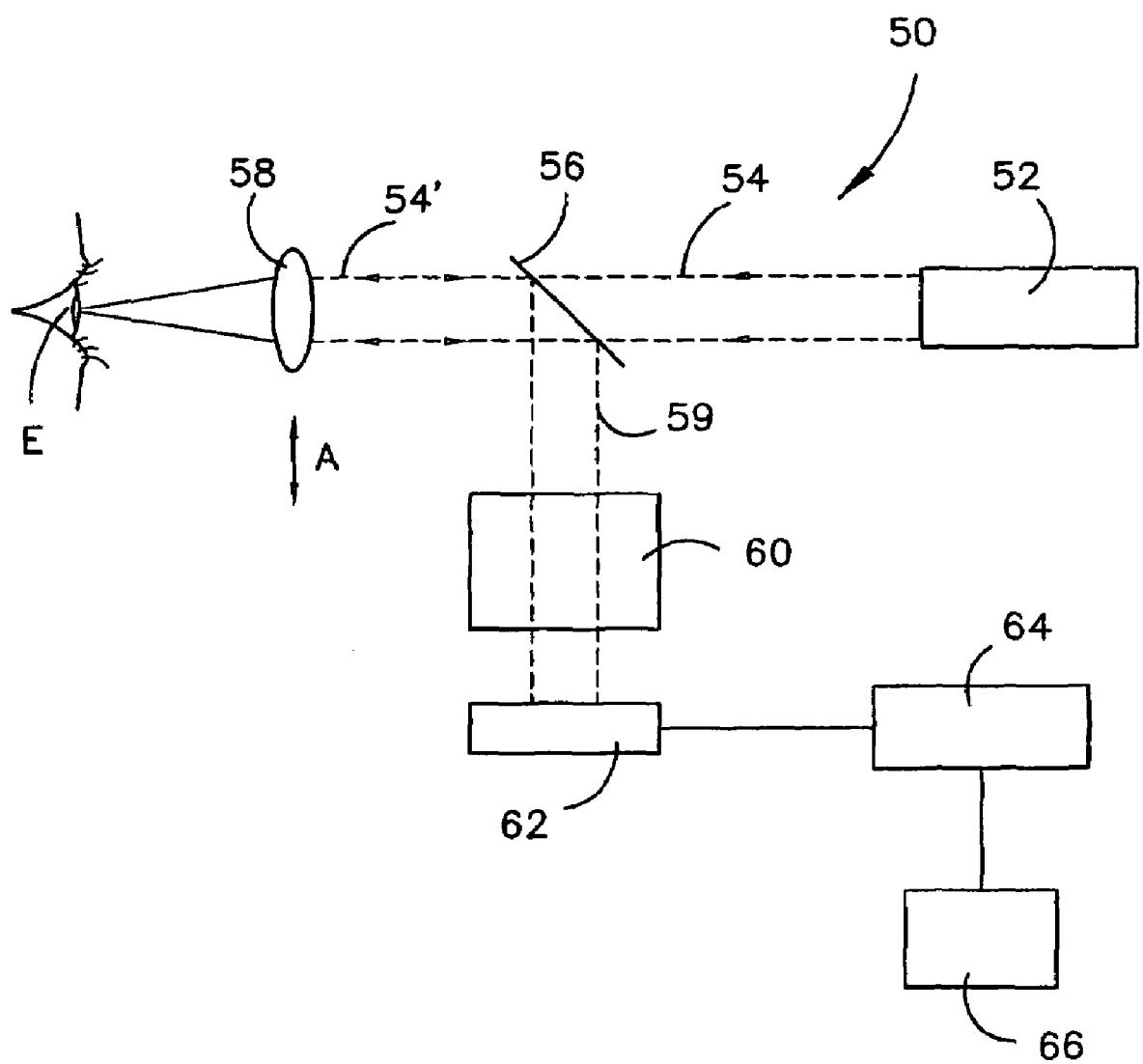
FIG. 5 is a schematic block diagram of a fundus camera according to the preferred embodiment of the invention.

In this aspect the apparatus is similar to that described with reference to FIG. 5 and the parallel beam of light 80 is shone through the eye E so that the light is detected by the detector 62. The processor 64 is stored with data relating to a planar wavefront so that the differences between the captured data and the stored planar data can be used to provide a measure of the amount of distortion or aberration introduced by the cornea 10 and lens 12. Once again, this is achieved by the detector 62 detecting the three images referred to above which enable the phase data to be generated and then comparing that phase data with phase data relating to the planar image so that a measure of the amount of distortion or aberrations introduced by the cornea 10 and lens 12 can be determined. This information can provide data for determining suitable spectacles or contact lens prescription or guiding a surgical procedure.

Since modifications within the spirit and scope of the invention may readily be effected by persons skilled within the art, it is to be understood that this invention is not limited to the particular embodiment described by way of example hereinabove.

In the claims which follow and in the preceding description of the invention, except where the context requires otherwise due to express language or necessary implication, the word "comprise", or variations such as "comprises" or "comprising", is used in an inclusive sense, i.e. to specify the presence of the stated features but not to preclude the presence or addition of further features in various embodiments of the invention.

The invention claimed is:

1. An apparatus for compensation for aberrations or distortions of an optical system, comprising:
   means for directing a beam of light through the optical system;
   detector means for detecting the beam of light at at least two different focal planes after the beam of light has passed through the optical system; and
   processing means for receiving data relating to the light at the two different focal planes from the detector and for processing the data to produce phase data relating to the wavefront of the beam of light emanating from the optical system by solving the transport of intensity equation to enable a transformation to be determined for transforming the data relating to the detected wavefront to a predetermined reference, and for applying the transformation to an image which has passed through the optical system to remove aberrations or distortions introduced by the optical system.

2. The apparatus of claim 1 wherein the detector comprises a charge coupled device.

3. The apparatus of claim 1 wherein the apparatus includes a light source for shining a parallel beam of light through the optical system and a beam splitter for directing reflected light from an article travelling back through the optical system to the detector for detection.

4. The apparatus of claim 1 wherein the apparatus includes a lens for focusing light passing through the optical system so as to obtain an image of an article viewed through the optical system.

5. The apparatus of claim 1 wherein the data to which the transformation is applied is intensity data.

6. The apparatus of claim 5 wherein the application of the transformation comprises a deconvolution of the intensity data.

7. The apparatus of claim 1 wherein the transformation is a propagation of the wave from one image location to another.

8. A method for compensating for aberrations or distortions in an optical system, comprising the steps of:
   shining light through the optical system;
   detecting the light at at least two different focal planes after the light has passed through the optical system;
   producing phase data relating to the wavefront of light detected by the detector at the two different focal planes by solving the transport of intensity equation;
   determining a transformation to transform the phase data in accordance with a known reference data;
   and applying the transformation to data relating to an image of an article produced through the optical system so as to remove the effects of aberrations or distortions of the optical system on that data.

9. The method of claim 8 wherein the data to which the transformation is applied is data relating to the image of the object so that the image of the object is produced free of distortions which would otherwise be introduced by the distortions or aberrations in the lens system.

10. The method of claim 8 wherein the detector comprises a charge coupled device.

11. The method of claim 8 wherein the data relating to the image is captured by directing a beam of light through apparatus including a lens for focusing light passing through the optical system so as to obtain an image of an article viewed through the optical system.

12. A fundus camera for producing an image of the fundus of a person's eye, said camera comprising:
   a detector for detecting at at least two different focal planes a beam of light passing through the cornea and lens of a person's eye and reflected from the fundus of the person's eye and again passing through the lens and cornea of the person's eye;
   processing means for determining phase data relating to the wavefront of the light beam detected by the detector at the two different focal planes by solving the transport of intensity equation and for producing a transformation required to convert the phase data from that detected by the detector to a known reference data;
   the detector also being for detecting a beam of light directed through a person's eye to obtain an image of the fundus and for producing phase data relating to that image; and
   the processing means being for processing the phase data relating to the image in accordance with the transformation to transform the data relating to the image to compensate for aberrations and distortions introduced by the cornea and lens of the person's eye, and for producing a image of the fundus, which is therefore free of distortions and aberrations introduced by the cornea and lens of the person's eye.

13. The camera of claim 12 wherein the camera also includes a light source for producing the beams of light detecting by the detector.

14. The camera of claim 12 wherein the camera further includes a lens for focusing the beam of light towards the eye so that the beam of light which produces the image is reflected from the fundus so as to provide an image of the fundus.

15. The camera of claim 12 wherein the camera has a monitor for displaying a image of the fundus.

16. Apparatus for determining the amount of distortion or aberration of a lens system, comprising:
   means for directing a beam of light through the optical system;
   detector means for detecting the beam of light at at least two different focal planes after the beam of light has passed through the optical system; and
   processing means for receiving data from the detector relating to the beam of light at the two different focal planes and for processing the data to produce phase data relating to the wavefront of the beam of light emanating from the optical system by solving the transport of intensity equation and for determining the amount of aberration or distortion of the lens system relative to reference phase data.

17. A method for determining aberrations or distortions in an optical system, comprising the steps of:
   shining light through the optical system;
   detecting the light at at least two different focal planes after the light has passed through the optical system;
   producing phase data relating to the wavefront of light detected by the detector at the two different focal planes by solving the transport of intensity equation; and
   comparing the phase data with a reference phase data to determine the difference and therefore the aberration or distortions introduced by the lens system.

* * * * *